US008962877B2

(12) United States Patent
Kohane et al.

(10) Patent No.: US 8,962,877 B2
(45) Date of Patent: Feb. 24, 2015

(54) METHOD OF MAKING ORGANOHALOSILANES

(75) Inventors: Joseph Peter Kohane, Indianapolis, IN (US); Unnikrishnan R. Pillai, Union, KY (US); Jonathan David Wineland, Bedford, KY (US)

(73) Assignee: Dow Corning Corporation, Midland, MI (US)

( * ) Notice: Subject to any disclaimer, the term of this patent is extended or adjusted under 35 U.S.C. 154(b) by 106 days.

(21) Appl. No.: 13/499,707

(22) PCT Filed: Jul. 28, 2010

(86) PCT No.: PCT/US2010/043492
§ 371 (c)(1),
(2), (4) Date: Apr. 2, 2012

(87) PCT Pub. No.: WO2011/046663
PCT Pub. Date: Apr. 21, 2011

(65) Prior Publication Data
US 2012/0197034 A1 Aug. 2, 2012

Related U.S. Application Data

(60) Provisional application No. 61/252,180, filed on Oct. 16, 2009.

(51) Int. Cl.
*C07F 7/16* (2006.01)
(52) U.S. Cl.
CPC ........................................ *C07F 7/16* (2013.01)
USPC .............................. 556/478; 556/472; 556/477
(58) Field of Classification Search
CPC .......... C07F 7/12; C07F 7/16; B01J 2231/323
USPC .......................................... 556/472, 477, 478
See application file for complete search history.

(56) References Cited

U.S. PATENT DOCUMENTS

| | | | |
|---|---|---|---|
| 2,403,370 A | 7/1946 | Hurd | |
| 2,427,605 A | 9/1947 | Hurd | |
| 4,602,101 A * | 7/1986 | Halm et al. | 556/472 |
| 4,973,725 A * | 11/1990 | Lewis et al. | 556/472 |
| 5,068,385 A | 11/1991 | Degen et al. | |
| 5,312,948 A | 5/1994 | Freeburne et al. | |
| 5,654,460 A | 8/1997 | Rong | |
| 5,880,307 A | 3/1999 | Daugherty et al. | |
| 2001/0020108 A1 | 9/2001 | Aramata et al. | |
| 2002/0183536 A1 | 12/2002 | Aramata et al. | |
| 2006/0084821 A1 | 4/2006 | Aramata et al. | |
| 2011/0158884 A1 * | 6/2011 | Bentley et al. | 423/342 |

FOREIGN PATENT DOCUMENTS

| | | |
|---|---|---|
| CN | 101456877 B | 5/2011 |
| EP | 0223447 | 2/1994 |
| WO | 2013093234 A1 | 6/2013 |

OTHER PUBLICATIONS

T.J. Wessel, D.G. Retwisch, Deactivation of CuSi and CuZnSnSi Due to Coke Formation, during the Direct Synthesis of Methylchlorosilanes, Journal of Catalysis 161, 861-866 (1996), A0248.
D. E. Kim, Effects of Al on the Diffusivity of Zn in the Cu—Zn—Al Alloy, Journal of the Korean Physical Society, vol. 14, No. 2, Sep. 1981.
G. Galvagnot, F. La Viat, F. Priolot, and E. Riminit, Diffusion and outdiffusion of aluminium implanted into silicon, Semicond. Sci. Technol. 8 (1993) 485-494.
K. H Brookes, et al., Effect of Al and Ca addition on the copper catalysed formation of silanes from Si and CH3Cl, Applied Catalysis A: General 206 (2001) 257-265.
W. Luo, et al., Effect of CuCl Particle Size on the Reduction Reaction by Silicon in Preparation of Contact Mass Used for Methylchlorosilane Synthesis, Ind. Eng. Chem. Res. 2006, 45, 129-133.
A. Laik , K. Bhanumurthy , G. B. Kale, Diffusion in Cu(Al) Solid Solution, Defect and Diffusion Forum vol. 279 (2008) pp. 63-69.
J. M. Bablin, A. C. Crawford, D. C. Demoulpied and L. N. Lewis, Effect of low Al silicon on the direct process, Ind. Eng. Chem. Res., 42 (2003) 3555-3565.
W. F. Banholzer and M. C. Burrell, XPS, Auger study of Cu3Si and its reaction with oxygen, Surf. Sci., 176 (1986) 125.
W. F. Banholzer and M. C. Burrell, Characterization of reactive areas in the direct process for the production of methylchlorosilanes, J. Catal., 114 (1988) 259-270.
H. Søerheim and H. A. Øye, The Role of Intermetallic Phases in the Direct Process to Methylchlorosilanes, Silicon Chem. Ind. II, Int. Conf., 2nd (1994), 81-92. Editor(s): Oeye, Harald A. Publisher: Tapir Forlag, Trondheim, Norway.
R. J. H. Voorhoeve, Organohalosilanes: Precursors to Silicones, Elsevier, Amsterdam 1967.
D. G. Rethwisch and J. F. Olakangil, Kinetics of coking in the Direct Process, Silicon for the Chemical Industry, V (2000), 399-405.
W. Luo, G. Wang, and J. Wang, Surface morphology and catalytic activity of the contact mass in organosilane synthesis,., Chem. Eng. Commun., 193 (2006) 754-763.
H. Souha, F. Bernard, E. Gaffet and B. Gillot, Reactivity of Cu3Si of different genesis towards copper (I) chloride, Thermochim. Acta, 351 (2000) 71-77.
F. Bernard, H. Souha and E. Gaffet, Enhancement of self-sustaining reaction Cu3Si phase formation starting from mechanically activated powders, Mater. Sci. Eng., A284 (2000) 301-306.

(Continued)

*Primary Examiner* — Sudhakar Katakam
*Assistant Examiner* — Pancham Bakshi
(74) *Attorney, Agent, or Firm* — Catherine U. Brown

(57) ABSTRACT

The invention pertains to a process for the preparation of organohalosilanes. The process comprises contacting a first finely-divided silicon comprising from 0.08 to 0.25% (w/w) of aluminum with an organohalide in a reactor at a temperature of from 250 to 350° C. in the presence of a Direct Process catalyst comprising copper, and a promotor; and introducing a second finely-divided silicon into the reactor comprising from 0.001 to <0.10% (w/w) of aluminum into the reactor as needed in an amount sufficient to maintain an aluminum concentration of from 0.08 to 0.2% (w/w), based on a weight of unreacted silicon and aluminum.

16 Claims, No Drawings

(56) References Cited

OTHER PUBLICATIONS

K. Bohmhammel, G. Roewer, I. Röver and J. Acker, Basic Reactions and Mechanisms of Processes Related to the Direct Synthesis, Silicon for the Chemical Industry, VII, MS Trollfjord, Tromso-Bergen, Norway (2004) 125-138.

Yuzhen, et. al., "Influence of the Quality of Silicon Powder on Synthesis Reaction of Methylchlorosilane", Silicone Material, 2007, pp. 134-137, vol. 21, Issue 3, Jilin, China.

Luo, et. al., "Effect and Role of Al Addition in the Direct Synthesis Reaction of Methylchlorosilane Monomer", Journal of Chemical Engineering of Chinese Universities, Dec. 2005, pp. 803-807, vol. 19, Beijing, China, Abstract considered.

* cited by examiner

METHOD OF MAKING ORGANOHALOSILANES

CROSS REFERENCE TO RELATED APPLICATIONS

This application is a U.S. national stage filing under 35 U.S.C. §371 of PCT Application No. PCT/US10/043492 filed on Jul. 28, 2010, currently pending, which claims the benefit of U.S. Provisional Patent Application No.61/252,180 filed Oct. 16, 2009 under 35 U.S.C. §119 (e). PCT Application No. PCT/US10/43492 and U.S. Provisional Patent Application No. 61/252,180 are hereby incorporated by reference.

FIELD OF THE INVENTION

The present invention relates to a method for the preparation of organohalosilanes and more particularly to a method comprising contacting a first finely-divided silicon with an organohalide in a reactor in the presence of a Direct Process catalyst and a promotor; and introducing a second finely-divided silicon into the reactor as needed in an amount sufficient to maintain an aluminum concentration in the reactor.

BACKGROUND OF THE INVENTION

Organohalosilanes are produced commercially by the "Direct Process". The Direct Process is well known in the art and comprises passing an organohalide such as methyl chloride, over silicon metal in the presence of a Direct Process catalyst and various promotors. The most important organohalosilane product of the Direct Process is dimethyldichlorosilane, although other components produced also find uses. In commercial processes of conducting the Direct Process, the reactor used is typically replenished continuously or semi-continuously with fresh silicon metal to replace the silicon metal that has reacted in the process. But, as the process progresses and progressively more fresh silicon is added, the selectivity for the diorganodihalosilane product and/or the silicon conversion eventually diminish. Once the selectivity and conversion diminish, the economics of carrying on the process become increasingly unacceptable, and the process is stopped. The remaining reactants are then removed from the reactor and disposed of, the reactor is replenished with fresh silicon, catalyst and promotor, and the process is reinitiated, which all add cost to the process. Consequently, there is a need for a method of preparing organohalosilanes by the Direct Process that reduces the frequency of reactor shutdowns by increasing the period that selectivity and conversion remain within acceptable ranges during a Direct Process campaign.

BRIEF SUMMARY OF THE INVENTION

The present invention is directed to a method of preparing organohalosilanes, the method comprising:
(i) contacting a first finely-divided silicon comprising from 0.08 to 0.25% (w/w) of aluminum with an organohalide in a reactor at a temperature of from 250 to 350° C. in the presence of a Direct Process catalyst comprising copper, and a promotor; and
(ii) introducing a second finely-divided silicon comprising from 0.001 to <0.10% (w/w) of aluminum into the reactor as needed in an amount sufficient to maintain an aluminum concentration of from 0.08 to 0.2 (w/w), based on a total weight of unreacted silicon and aluminum.

The method of the present invention prolongs the bed life in the Direct Process by prolonging the period that selectivity and conversion are maintained within acceptable limits. Further, the method reduces the production costs associated with the Direct Process by reducing the frequency of shutdown, clean-out, disposal, and start-up cycles. Still further, the method reduces the coking in the reactor. Additionally, the method reduces the deposition of metallic copper in the reaction bed.

The organohalosilanes produced by the present method are the precursors of most of the products in the silicone industry. For example, dimethyldichlorosilane may be hydrolyzed to produce linear and cyclic polydimethylsiloxanes. Other organohalosilanes may also be used to make other silicon-containing materials such as silicone resins or sold into a variety of industries and applications.

DETAILED DESCRIPTION OF THE INVENTION

A method of preparing organohalosilanes according to the present invention comprises:
(i) contacting a first finely-divided silicon comprising from 0.08 to 0.25% (w/w) of aluminum with an organohalide in a reactor at a temperature of from 250 to 350° C. in the presence of a Direct Process catalyst comprising copper, and a promotor; and
(ii) introducing a second finely-divided silicon comprising from 0.001 to <0.10% (w/w) of aluminum into the reactor as needed in an amount sufficient to maintain an aluminum concentration of from 0.08 to 0.2% (w/w), based on a total weight of unreacted silicon and aluminum.

In step (i) of the method of preparing organohalosilanes, a first finely-divided silicon comprising from 0.08 to 0.25% (w/w) of aluminum is contacted with an organohalide in a reactor at a temperature of from 250 to 350° C. in the presence of a Direct Process catalyst comprising copper, and a promotor.

The first finely-divided silicon comprises from 0.08 to 0.25% (w/w), alternatively from 0.10 to 0.16% (w/w), alternatively from 0.10 to 0.14% (w/w), aluminum. The % aluminum can be determined by, for example, X-ray fluorescence, inductively coupled plasma-atomic emission spectrometry (ICP-AES), and atomic absorption spectrometry.

The first finely-divided silicon comprises from 95 to 99.92% (w/w), alternatively from 97.5 to 99.92% (w/w), alternatively from 99.0 to 99.92% (w/w), silicon.

The first finely-divided silicon may comprise other elements such as Fe, Ca, Ti, Mn, Zn, Sn, Pb, Bi, Sb, Ni, Cr, Co, and Cd and their compounds as impurities. Each of these elements are typically present from 0.0005 to 0.6% (w/w) based upon the total weight of the first finely-divided silicon.

The first finely-divided silicon has a maximum particle size diameter up to 200 µm, alternatively up to 85 µm; alternatively up to 50 µm.

The first finely-divided silicon typically has a particle size mass distribution characterized by a $10^{th}$ percentile of 1 to 6 µm, a $50^{th}$ percentile of 5 to 25 µm, and a $90^{th}$ percentile of 25 to 60 µm; alternatively a $10^{th}$ percentile from 1 to 6 µm, a $50^{th}$ percentile from 7 to 25 µm, and a $90^{th}$ percentile from 30 to 60 µm; alternatively a $10^{th}$ percentile from 2.1 to 6 µm, a 50th percentile from 10 to 25 µm, and a $90^{th}$ percentile from 30 to 45 µm; alternatively a $10^{th}$ percentile from 2.5 to 4.5 µm, a $50^{th}$ percentile from 12 to 25 µm, and a $90^{th}$ percentile from 35 to 45 µm.

As used herein, "silicon particle size distribution" is characterized by three percentile sizes. Each percentile describes the particle size diameter in microns below which a mass percentage of the size distribution resides. For instance, "$10^{th}$ percentile" means that 10% of the mass distribution is smaller than the $10^{th}$ percentile size; "$50^{th}$ percentile" means that 50% of the mass distribution is smaller than the $50^{th}$ percentile size; and "$90^{th}$ percentile" means 90% of the mass distribution is smaller than the $90^{th}$ percentile size. It is noted that the "particle size mass distribution" is given by a mass based particle size distribution as measured by sedimentation techniques, or through laser diffraction/scattering processes with appropriate correction to sedimentation techniques using particle size standards.

Examples of the first finely-divided silicon include, but are not limited to, chemical and metallurgical grade silicon having an aluminum percent within the ranges described and exemplified above. Chemical grade silicon and metallurgical grade silicon are available commercially.

Blends of silicon batches and/or grades may be used for the first finely-divided silicon, even those containing less than the described % aluminum, as long as the % aluminum of the combined batches and/or grades is within the ranges defined and exemplified above. Also, batches of silicon having lower aluminum % than described for the first finely-divided silicon may be used to make the first finely divided silicon by adding aluminum to the batch to bring the aluminum % within the ranges described above. Blending of batches of silicon and adding aluminum to silicon is typically done with mixing. Standard techniques, such as vibration or stirring, may be used to conduct the mixing.

The first finely-divided silicon having a particle size and particle size mass distribution described above may be produced by standard methods for producing particulate silicon from bulk silicon, such as silicon ingots. For example, attrition, impact, crushing, grinding, abrasion, milling, or chemical methods may be used. Grinding is typical. The particulate silicon may be further classified as to particle size distribution by means of, for example, screening or by the use of mechanical aerodynamic classifiers such as a rotating classifier.

The aluminum in the first finely-divided silicon may be present in the form of metallic aluminum, aluminum halide, aluminum oxide, aluminum alloys, aluminum-containing silicon alloys, aluminum carbide, or other solid compounds containing aluminum.

Examples of suitable forms of aluminum include aluminum powder, $AlCl_3$, Si—Al alloy, Al—Cu alloy, $FeAl_2Si_2$, $Si_5Ca_{20}Al_{0.1}$, $Al_2CaSi_2$, $Al_6CaFe_4Si_8$, $Al_8Fe_5Si_7$, $Al_9Fe_5Si_8$, and $Fe_4Si_6Al_4Ca$.

The aluminum may be a single form or may be a mixture of forms and/or compounds of aluminum.

The organohalide has the formula RX (I), wherein R is hydrocarbyl and X is halo. X is selected from chloro, bromo, iodo, and fluoro.

The hydrocarbyl groups represented by R in formula (I) typically have from 1 to 10 carbon atoms, alternatively from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl, cyclohexyl, and methylcyclohexyl; aryl, such as phenyl and naphthyl; alkaryl, such as tolyl, and xylyl; aralkyl such as benzyl and phenylethyl; alkenyl, such as vinyl, allyl, and propenyl; aralkenyl, such as styryl and cinnamyl; and alkynyl, such as ethynyl and propynyl.

Examples of organohalides include, but are not limited to, chlorobenzene, bromobenzene, methyl chloride, methyl bromide, ethyl chloride and ethyl bromide.

Methods of preparing organohalides are well known in the art; many of these compounds are commercially available.

The Direct Process catalyst comprises copper. Any form of copper may be used, for example, elemental copper, copper alloys, copper compounds and mixtures thereof.

Examples of the Direct Process catalyst comprising copper include, but are not limited to, granular copper powder, stamped copper, Cu—Zn alloy, Cu—Si alloy, Cu—Sb alloy, cuprous oxide, cupric oxide, cupric chloride, cuprous chloride, copper nitride, copper hydroxide, copper formate, and mixtures of at least two of the preceding catalysts.

Methods of making Direct Process catalysts comprising copper are well known in the art; most of these compounds are available commercially.

The promotor can be any element or its compounds that accelerate or catalyse the Direct Process. Promotors include, but are not limited to, phosphorous, phosphorous compounds, zinc, zinc compounds, tin, tin compounds, antimony, antimony compounds, arsenic, arsenic compounds, cesium, cesium compounds, aluminum and aluminum compounds and mixtures of at least two of the preceding promotors.

The promotor comprises one or more elements selected from zinc, tin, antimony, arsenic, cesium, phosphorous and aluminum.

Examples of such promotor materials are described in, for example, U.S. Pat. Nos. 4,602,101, 4,946,978, 4,762,940, and U.S. Re. 33,452. Many promotors are available commercially.

Step (i) of the process can be carried out in a suitable reactor for conducting the Direct Process. For example, a fixed bed, a stirred bed, and fluidized bed reactor may be used. Fluidized bed reactors are typically utilized on commercial scale.

Step (i) of the process is typically run at atmospheric pressure conditions or slightly above atmospheric pressure conditions.

The reactants of step (i) are typically agitated during the method. Agitation of the reactants in step (i) is typically accomplished within a fluidized bed reactor. When the reaction is carried out in a reactor other than a fluidized bed reactor, agitation may be accomplished by, for example, vibration or mechanical mixing.

The first finely-divided silicon, catalyst and promotor, may be contacted in any order in the initial charge before the organohalide is introduced. The organohalide is then introduced to the reactor to start the reaction.

When using a fluidized bed, the organohalide, or a mixture of the organohalide and an inert gas, is introduced into the reactor bed at a rate sufficient to fluidize the bed but below a rate that will completely elutriate the bed. The rate will depend upon the particle size mass distribution of the silicon in the bed and the dimensions of the fluidized bed reactor. One skilled in the art would know how to determine a sufficient rate of organohalide, or organohalide and inert gas, addition to fluidize the bed while not completely elutriating the material from the bed. Examples of the inert gas include nitrogen, helium, argon and mixtures thereof. When not using a fluidized bed, the rate at which the organohalide is added to the bed is typically selected to optimize silicon reactivity.

The temperature at which the first finely-divided silicon, catalyst, promotor and organohalide are contacted is from 250 to 350° C., alternatively from 280 to 340° C.

The concentration of the Direct Process catalyst comprising copper is typically from 0.1 to 10 parts by weight copper, alternatively from 2 to 8 parts by weight copper, alternatively from 5 to 8 parts by weight copper, per 100 parts by weight of the first finely-divided silicon.

The concentration, based on the weight of the first finely-divided silicon, of the promoter is typically such that one or more of the following elements is in the following amounts: 50 to 10,000 parts per million (ppm) zinc; 5 to 200 ppm tin, antimony or arsenic; 10 to 1000 ppm cesium; 25 to 2,500 ppm phosphorous; 200 to 2,500 ppm aluminum.

In step (ii) of the method of preparing organohalosilanes, a second finely-divided silicon comprising from 0.001 to <0.10% (w/w) of aluminum is introduced into the reactor as needed in an amount sufficient to maintain an aluminum concentration of from 0.08 to 0.2% (w/w), based on a total weight of unreacted silicon and aluminum.

The second finely-divided silicon comprises from 0.001 to <0.10% (w/w), alternatively from 0.01 to 0.08% (w/w), alternatively from 0.02 to 0.05% (w/w), aluminum.

The second finely-divided silicon comprises from 95 to <100% (w/w), alternatively from 98 to <100% (w/w), alternatively from 99 to 99.99% (w/w), silicon.

The second finely-divided silicon may comprise other elements as described for the first finely-divided silicon.

The particle size and particle size mass distribution of the second finely-divided silicon are characterized as defined for the first finely-divided silicon.

Examples of the second finely-divided silicon include, but are not limited to, solar and electronics grade silicon having an aluminum % within the ranges described and exemplified above. Solar grade and electronics grade silicon are known in the art and are available commercially.

Blends of silicon batches and/or grades, even batches or grades containing an aluminum percent outside of the limits described and exemplified above for the second finely-divided silicon, may be used to produce the second finely-divided silicon as long as the % aluminum of the combined batches and/or grades is within the ranges defined and exemplified above.

The particle size and particle size mass distribution of the second finely-divided silicon may be produced as described and exemplified above for the first finely-divided silicon above.

The aluminum in the second finely-divided silicon is as described and exemplified above for the first finely-divided silicon.

Step (ii) of the method may be carried out in a reactor as described and exemplified above for step (i) of the method.

In step (ii), the second finely-divided silicon is introduced into the reactor as needed to maintain an aluminum concentration from 0.08 to 0.2% (w/w), based on a total weight of unreacted silicon and aluminum. As used herein, "as needed" means that the second finely-divided silicon is added continuously or periodically to the reactor to maintain the desired aluminum concentration in the reactor. For example, when a fixed or stirred bed is used, the second finely-divided silicon is typically added after some percent of the silicon in the reactor has reacted with the organohalide. In some cases, the second finely-divided silicon may be added when most of the silicon in the reactor has reacted. However, when a fluidized bed reactor is utilized, silicon is typically introduced to the reactor continuously, and the rate of silicon addition is equal to, or almost equal to, the rate at which the silicon and organohalide react.

The second finely-divided silicon is introduced into the reactor as needed in an amount sufficient to maintain an aluminum concentration of from 0.08 to 0.2% (w/w), alternatively from 0.08 to 0.15% (w/w), alternatively from 0.10 to 0.15% (w/w), based on a total weight of unreacted silicon and aluminum. As used herein, "unreacted silicon and aluminum" means all silicon in the reactor from the first and second finely-divided silicon that has not reacted with the organohalide and all aluminum in the reactor in any form.

The weight of unreacted silicon may be determined from the difference between the weight of silicon added to the reactor as the first and second finely-divided silicon and the weight of silicon in the organohalosilanes produced by the method. Additionally, the amount of silicon in the reactor may be determined by weighing the reactor.

The aluminum concentration may be determined by, for example, obtaining a sample of the silicon in the reactor and measuring the aluminum in the sample by X-ray fluorescence, X-ray diffraction, plasma emission spectroscopy, or atomic absorption spectrometry.

As used herein, "an amount sufficient" means an amount that will not cause the concentration of aluminum in the reactor to either fall below or rise above the desired concentration in the reactor but, instead, will maintain an aluminum concentration inside of the desired ranges described and exemplified above. Typically, an amount sufficient is from 1 to 100% (w/w), alternatively from 20 to 80% (w/w), alternatively from 30 to 60% (w/w), of all silicon added to replenish the reactor. Alternatively, the amount sufficient can be calculated using a point within the desired aluminum concentration range and then back-calculating for the amount of second finely-divided silicon to add using the desired aluminum concentration in the reactor, the rate of addition or weight of silicon to replenish the reactor, the weight of the unreacted silicon, and the % aluminum in the second finely-divided silicon.

The second finely-divided silicon may be introduced by itself or simultaneously, staggered, or alternated with the introduction of additional first finely-divided silicon.

The method may further comprise continuing the introduction of the second finely-divided silicon until the selectivity or silicon conversion are outside of acceptable limits. The acceptable limits are where the economics of the process begin to become unfavorable. Typically, the second finely divided silicon is introduced until the selectivity is above 0.35 or the silicon conversion is below 50%, alternatively until the selectivity is above 0.20 and the silicon conversion is below 65%, alternatively until the selectivity is above 0.10 and the silicon conversion is below 80%. As used herein, "selectivity" means the weight ratio of organotrihalosilane (e.g., methyltrichlorosilane) to diorganodihalosilane (e.g., dimethyldichlorosilane) produced by the process of the invention. As used herein, "silicon conversion" is the total weight of silicon reacted divided by the cumulative weight of silicon fed to the reactor multiplied by 100.

The method may further comprise pre-heating and gasifying, when a liquid, the organohalide before it is introduced into the reactor.

The method may further comprise pre-heating the first and/or second finely-divided silicon in an inert atmosphere and at a temperature up to 350° C., alternatively 200 to 280° C., prior to contacting with the organohalide.

The method may further comprise (iii) introducing additional first finely-divided silicon into the reactor before, during or after step (ii) to replenish the reactor with silicon and replace silicon that has reacted with the organohalide.

The method may further comprise maintaining the level of catalyst and promotor in the reactor at, or close to, the levels described above for step (i). The catalyst and promotor levels are typically maintained by introducing new catalyst and promotor into the reactor together with the second finely-divided silicon added to replenish the reactor with silicon. Catalyst and promoter levels in the reactor may be determined using the same test methods as described for determining the aluminum concentration in the first and second finely divided silicon.

The method may further comprise removing the organohalosilane from the reactor in the form of a gas and condensing the gas to form a liquid. The method may further comprise separation of a mixture of organohalosilane products by, for example, distillation.

The organohalosilanes prepared according to the present method typically have the formula $R_aH_bSiX_{4-a-b}$ (II), wherein R is hydrocarbyl and X is halo. The hydrocarbyl groups represented by R and the halo groups represented by X are as described and exemplified above for the organohalide.

In formula (II), the subscript "a" has a value of 1, 2, or 3; "b" has the value 0, 1, or 2, alternatively 0, or 1; and a+b has the value 1, 2, or 3.

Examples of organohalosilanes prepared according to the present method include, but are not limited to, dimethyldichlorosilane (i.e., $(CH_3)_2SiCl_2$), dimethyldibromosilane, diethyldichlorosilane, diethyldibromosilane, trimethylchlorosilane (i.e., $(CH_3)_3SiCl$), methyltrichlorosilane (i.e., $(CH_3)SiCl_3$), dimethylchlorosilane (i.e., $(CH_3)_2HSiCl$), methyldichlorosilane (i.e., $(CH_3)HSiCl_2$), methylchlorodihydrosilane, phenyltrichlorosilane, diphenyldichlorosilane, and triphenylchlorosilane. The method may also produce small amounts of halosilane and organosilane products such as tetramethylsilane, trichlorohydrosilane, and tetrachlorosilane.

The method of the present invention prolongs the bed life in the Direct Process by prolonging the period that selectivity and conversion are maintained within acceptable limits. This prolonged bed life results in an increase in silicon bed volume reactivity by a factor of from 1.3 to 1.5, compared to a similar processes not of the invention; an increase in percent yield of diorganodihalosilane of from 2 to 3%, based on the weight of diorganodihalosilane typically produced by a processes not of the invention; and a decrease in yield of organotrihalosilane of from 10 to 12%, based on the weight of organotrihalosilane typically produced by a processes not of the invention. As used herein, "silicon bed volume reactivity" means the volume of silicon that can be reacted in a Direct Process campaign before shutdown. Further, the method reduces the production costs associated with the Direct Process to produce an organohalosilane by reducing the frequency of shutdown, clean-out, disposal, and start-up cycles. Still further, the method reduces the coking in the reactor. Additionally, the method reduces the deposition of metallic copper in the reaction bed. However, every embodiment of the present invention is not intended to possess every benefit herein discussed.

The organohalosilanes produced by the present method are the precursors of most of the products in the silicone industry. For example, dimethyldichlorosilane may be hydrolyzed to produce linear and cyclic polydimethylsiloxanes. Other organohalosilanes may also be used to make other silicon-containing materials such as silicone resins or sold into a variety of industries and applications.

EXAMPLES

The following examples are included to demonstrate embodiments of the method of the invention. However, those of skill in the art should, in light of the present disclosure, appreciate that many changes can be made in the specific embodiments which are disclosed and still obtain a like or similar result without departing from the spirit and scope of the invention. All percentages are in wt. % unless otherwise noted.

Three different types of silicon samples were used in the examples: (i) chemical or technical grade (C—Si) containing 98.5% silicon; (ii) hyper-pure silicon (E-Si) containing 99.99% silicon; and (iii) low aluminum silicon (low Al Si) containing 99% silicon. The % aluminum of the three silicon samples are given in Table 1. The C—Si is representative of the first finely-divided silicon, and the hyper-pure Si and low Al Si are representative of the second finely-divided silicon.

TABLE 1

Aluminum composition of various silicon samples used

| Name | Notation | Aluminum % (w/w) |
|---|---|---|
| Hyper-pure Si | E-Si | 0.0029 |
| Low Al Si | LAlSi | 0.02 |
| C—Si | C—Si | 0.12 |

The weight of organohalosilanes produced in the examples was determined using a Hewlett Packard Gas Chromatograph using a RTX 40% TFP (0.18 mm×40 m) column under a temperature programmed mode in the range 40-250° C. The selectivity (T/D ratio) in the examples is the weight ratio of $(CH_3)SiCl_3$ to $(CH_3)_2SiCl_2$.

Silicon conversion was determined by, for examples 1 and 2, silicon weight loss from the reactor at the end of the reaction divided by the weight of silicon added to the reactor multiplied by 100 and, for examples 3, 4, and 5, the difference between the amount of Si fed to the reactor and the amount of Si in the products formed divided by the total amount of silicon fed to the reactor multiplied by 100.

Concentration of aluminum in silicon was determined by inductively coupled plasma-atomic emission spectrometry (ICP-AES). The method used a typical procedure known for elemental analysis of solid samples, wherein the solids were dissolved in HF and the concentration in aqueous solution determined with respect to appropriate standards containing known amounts of the elements of interest.

Percentage carbon was determined by a commercial Carbon-Analyzer (Leco) using a procedure for carbon analysis of solid samples involving the determination of the amount of $CO_2$ gas generated by high temperature oxidation of the material in an oxygen environment and comparing the results to a standard containing known amount of carbon.

Example 1 (Comparative Example)

In a vibrating carbon steel tubular reactor (12" long, 0.5" I.D.), 38.4 g of ground Si were mixed with a copper catalyst and promotor, as previously herein described, under inert conditions. The reactor with the reaction mass was preheated in nitrogen flow at 250° C. for 30 minutes. After the pretreatment, the temperature was increased to 320° C. and methyl chloride (MeCl) was introduced at a flow rate of 10 $gh^{-1}$. Three grades of silicon were tested: (i) chemical grade Si (C—Si), (ii) hyper-pure Si (E-Si), and (iii) hyper-pure Si (E-Si) with Al added with the copper catalyst to bring the aluminum concentration to 0.12wt % Al (w/w). Silicon (i) and (iii) are examples of the first finely-divided silicon.

The reaction products were collected in a dry ice-acetone cooled trap at various time intervals and analyzed by a Hewlett Packard Gas Chromatograph using a RTX 40% TFP (0.18 mm×40 m) column under a temperature programmed mode in the range 40-250° C. The results of the reactions after 20 hours are shown in Table 2. This example demonstrate the importance of initiating the Direct Process reaction with the aluminum concentration of the first finely-divided silicon for optimum selectivity and silicon conversion and that Al may be added to form the first finely-divided silicon.

TABLE 2

Comparison of runs made starting with various levels of aluminum.

| Silicon | Aluminum (%) (w/w) | Silicon Conversion (%) | Selectivity Ratio (T/D) |
|---|---|---|---|
| C—Si | 0.12 | 65 | 0.05 |
| E-Si | 0.0029 | 22 | 0.097 |
| E-Si + Al added | 0.12 | 67 | 0.04 |

Example 2 (Comparative Example)

Reactions were performed in a similar way as described in Example 1 using low Al Si with Al added as part of the catalyst package. The results in Table 3 show lower silicon conversion for low Al Si but comparable or better silicon conversion and selectivity for the Al-added low Al Si compared to that of chemical grade Si. This example demonstrate the importance of initiating the Direct Process reaction with the aluminum concentration of the first finely-divided silicon for good selectivity and silicon conversion and that Al may be added to form the first finely-divided silicon.

TABLE 3

Comparison of performance of silicon with varying aluminum content.

| Silicon | Aluminum (%) | Silicon Conversion (%) | Selectivity Ratio (T/D) |
|---|---|---|---|
| C—Si | 0.12 | 65 | 0.05 |
| Low Al Si | 0.02 | 31 | 0.07 |
| Low Al Si with Al added | 0.12 | 67 | 0.04 |

Example 3 (Comparative) and Example 4

Continuous reaction studies up to 72 hours in duration were conducted in a vibrating bed reactor as described in example 1 with continuous silicon feed through a hopper/reservoir. Both example 3 and 4 were initiated with C—Si (first finely-divided silicon) comprising 0.12% aluminum. In example 3, the reactor was replenished with C—Si. In example 4, the reactor was replenished with low Al Si (second finely-divided silicon). The results in Table 4 show that selectivity is maintained longer for the reaction where C—Si (the first finely-divided silicon) was used for reaction initiation, but the reactor was replenished with low Al Si (the second finely-divided silicon). Table 5 shows the aluminum content of the unreacted silicon in the bed at the end of the experiment. The end aluminum concentration of the reaction bed was greater for the reaction using only C—Si, and the end aluminum concentration for the reaction using C—Si initiation followed by reactor replenishment with low Al Si was close to the value of the C—Si used for initiation of 0.12% (w/w).

TABLE 4

Selectivity at various reaction intervals for reaction using only C—Si (first finely-divided silicon) and for reaction using C—Si (first finely-divided silicon) for initiation followed by low Al Si (second finely-divided silicon) addition.

| Example No. | Silicon | Selectivity Ratio (T/D) after Reaction Run Time (hrs.) | | | | | | | | |
|---|---|---|---|---|---|---|---|---|---|---|
| | | 4 | 20 | 24 | 28 | 44 | 48 | 52 | 68 | 72 |
| 3* | C—Si (first finely-divide) | 0.04 | 0.04 | 0.04 | 0.05 | 0.05 | 0.06 | 0.06 | 0.08 | 0.24 |
| 4 | C—Si initiation followed by low Al Si (second finely-divided) | 0.06 | 0.045 | 0.03 | 0.03 | 0.03 | 0.03 | 0.03 | 0.03 | 0.03 |

*Comparative Example.

TABLE 5

Start and end Al concentration for examples 3 and 4.

| Example No. | Silicon | Start Al % (w/w) | End Al % (w/w) |
|---|---|---|---|
| 3* | C—Si (first finely-divided) | 0.12 | 0.2203 |
| 4 | C—Si initiation followed by low Al Si (second finely-divided) | 0.12 | 0.1181 |

*Comparative Example.

Example 4 demonstrates that selectivity is superior when the method of the invention is followed and that adding the second finely-divided silicon will maintain the aluminum concentration in the unreacted silicon.

Example 5

A continuous reaction was conducted for 72 hours in a vibrating bed reactor with continuous silicon feed from a hopper/reservoir and with catalyst and promotor as described in example 1. The second finely-divided Si was added via the hopper reservoir to the reaction bed to compensate for the reacted Si in an automated mode. The reaction was initiated with C—Si (first finely-divided silicon) and replenished with the second finely divided silicon comprising a mixture of C—Si and low Al Si in a weight ratio of 1:3 and having a combined % aluminum of 0.053% (w/w).

Results after 72 hours are in Table 6 along with the results from example 3. The results include the end aluminum weight % of unreacted silicon, the final Selectivity Ratio, and the end carbon weight %, based on the unreacted silicon. The results show, in addition to the maintenance of aluminum concentration, better Selectivity Ratio (T/D) and lower weight %, based on the weight of unreacted silicon, carbon than the C—Si (first finely-divided silicon) only run of Comparative Example 3.

TABLE 6

Aluminum concentration, Selectivity Ratio, and carbon weight % of unreacted silicon after a 72 hour reaction.

| Example | Silicon Description | Starting Al % | End Al % of unreacted silicon | Ending Selectivity Ratio (T/D) | End C % |
|---|---|---|---|---|---|
| 5 | C—Si followed by second finely-divided silicon (blend) | 0.12 | 0.118 | 0.044 | 0.37 |
| 3 (comparative) | C—Si only | 0.12 | 0.220 | 0.24 | 1.45 |

Example 5 shows that aluminum concentrations in the unreacted silicon may be maintained by adding second finely-divided silicon, that blends of silicon with varying aluminum contents may be used as the second finely-divided silicon, and that, compared to Example 3, selectivity and coking (% C) is improved when the reactor is replenished with second finely-divided silicon rather than only first finely-divided silicon.

We claim:

1. A method of preparing organohalosilanes, the method comprising:
   (i) contacting a first finely-divided silicon comprising from 0.08 to 0.25% (w/w) of aluminum with an organohalide in a reactor at a temperature of from 250 to 350° C. in the presence of a Direct Process catalyst comprising copper, and a promotor; and
   (ii) introducing a second finely-divided silicon comprising from 0.001 to <0.10% (w/w) of aluminum into the reactor as needed in an amount sufficient to maintain an aluminum concentration from 0.08 to 0.2% (w/w), based on a total weight of unreacted silicon and aluminum.

2. The method of claim 1 wherein the method produces organohalosilanes characterized by the formula $R_aH_bSiX_{4-a-b}$ (II), wherein R is hydrocarbyl, X is halo, a has a value of 1, 2, or 3; b has the value of 0, 1, or 2; and a+b has a value of 1, 2, or 3.

3. The method of claim 2, wherein the organohalide is characterized by the formula RX (I), wherein R is hydrocarbyl and X is halo.

4. The method of claim 3 wherein the R is alkyl.

5. The method of claim 1, wherein the catalyst comprising copper is selected from granular copper powder, stamped copper, Cu—Zn alloy, Cu—Si alloy, Cu—Sb alloy, cuprous oxide, cupric oxide, cupric chloride, cuprous chloride, copper nitride, copper hydroxide, and copper formate.

6. The method of claim 5 wherein the catalyst is from 0.01 to 10 parts by weight copper per 100 parts by weight of the first finely-divided silicon.

7. The method of claim 1 wherein the first and second finely-divided silicon have a maximum particle size diameter up to 200 μm and a particle size mass distribution characterized by a $10^{th}$ percentile of 1 to 6 μm, a $50^{th}$ percentile from 5 to 25 μm, and a $90^{th}$ percentile of 25 to 60 μm.

8. The method of claim 1, wherein the promotor is selected from phosphorous, phosphorous compounds, zinc, zinc compounds, tin, tin compounds, antimony, antimony compounds, arsenic, arsenic compounds, cesium, cesium compounds, aluminum and aluminum compounds.

9. The method of claim 1, wherein the reactor is a fluidized bed reactor.

10. The method of claim 9, wherein the second finely-divided silicon is introduced into the fluidized bed reactor continuously.

11. The method of claim 9, wherein the bed of the fluidized bed reactor is fluidized with the organohalide or a mixture of the organohalide and an inert gas.

12. The method of claim 1, wherein the contacting of the first finely-divided silicon comprising from 0.08 to 0.25% (w/w) of aluminum with the organohalide in the reactor is at a temperature of from 280 to 340°C.

13. The method of claim 2, wherein the second finely-divided silicon is introduced until the organohalosilanes are produced with a selectivity above 0.20 or a silicon conversion below 65%.

14. The method of claim 1, further comprising: (iii) introducing additional first finely-divided silicon before, during or after step (ii).

15. The method of claim 1, wherein the second finely-divided silicon is introduced until selectivity is above 0.35, where selectivity means weight ratio of organotrihalosilane to diorganodihalosilane produced.

16. The method of claim 1, wherein the second finely-divided silicon is introduced until selectivity is above 0.10 and the silicon conversion is below 80%, where selectivity means weight ratio of organotrihalosilane to diorganodihalosilane produced, and where silicon conversion is total weight of silicon reacted divided by cumulative weight of silicon fed to the reactor multiplied by 100.

* * * * *